United States Patent [19]

Hatsuwi

[11] Patent Number: 5,193,541
[45] Date of Patent: Mar. 16, 1993

[54] HEALTH EXAMINATION METHOD AND SYSTEM USING PLURAL SELF-TEST STATIONS AND A MAGNETIC CARD

[76] Inventor: Ryotaro Hatsuwi, 7, Nanasegawa-cho, Takeda, Fushimi-ku, Kyoto-shi, Japan

[21] Appl. No.: 618,508

[22] Filed: Nov. 28, 1990

[30] Foreign Application Priority Data

Dec. 5, 1989 [JP] Japan .................. 1-317040

[51] Int. Cl.$^5$ ............................................. A61B 10/00
[52] U.S. Cl. ..................................... 128/630; 128/906
[58] Field of Search ............... 128/630, 670, 711, 906; 364/413.06

[56] References Cited

U.S. PATENT DOCUMENTS

| | | | |
|---|---|---|---|
| 3,566,370 | 2/1971 | Worthington, Jr. et al. | 128/906 |
| 3,857,383 | 12/1974 | Sommerfeld et al. | 128/906 |
| 4,033,336 | 7/1977 | Murawski et al. | 128/711 |
| 4,852,570 | 8/1989 | Levine | 128/906 |

OTHER PUBLICATIONS

Yamaguchi, K., "The Toshiba Multiphasic Health Screening Centre", *Medical & Biological Engineering*, vol. 9, No. 5, Sep. 1971, pp. 421–429.

*Primary Examiner*—William E. Kamm
*Attorney, Agent, or Firm*—Wenderoth, Lind & Ponack

[57] ABSTRACT

A health examination is conducted using a minimal number of staff members by issuing a patient a magnetic card and a questionnaire and having the patient conduct a plurality of health related self-test measurements at respective automated test stations. The results of the self-test measurements are recorded on the magnetic card at each automated test station. When the plurality of self-test measurements are completed, the data recorded on the magnetic card is read and a diagnosis is effected based on the thus read data and the contents of the questionnaire completed by the patient. Then, a permanent record is made of the diagnosis and the results of the self-test measurements.

14 Claims, 1 Drawing Sheet

HEALTH EXAMINATION METHOD AND SYSTEM USING PLURAL SELF-TEST STATIONS AND A MAGNETIC CARD

BACKGROUND OF THE INVENTION

1. Field of the Invention

The present invention relates to a high-speed and labor-saving health examination method and system in which a periodic health examination is carried out using various automated measuring instruments operated by the person to be examined according to predetermined operation instructions.

Measured data generated by each of the measuring instruments is stored on a plastic magnetic stripe card. The magnetic card is then insert into a reader to display the stored contents thereof. A comprehensive diagnosis is performed by a doctor using the displayed measured data, a permanent examination card and a questionnaire completed by the person to be examined before the examination. The diagnosis is printed out on the examination card and optionally stored in a storage medium disc. According to the present invention, in the case of a periodic health examination, the number of persons required to conduct the examination is reduced considerably. Further, manual recording is eliminated and the time required for the various examinations is reduced to speed up and improve the efficiency and accuracy of the examination.

2. Prior Art

Conventionally, when a periodic health examination conforming to local safety and health laws is carried out, various measurements are conducted with respect to height, weight, blood pressure, eyesight, hearing, urine content and so on. At least two persons, one for conducting the measurement and one for recording the results, are required for each measuring station. That is, for example, ten attendants are necessary for measuring and recording the five examinations related to height, weight, blood pressure, eyesight, hearing and urine content. In addition, a radiographer, a doctor and a nurse are necessary for a chest x-ray examination. Thus, as many as thirteen persons are required in all, and hence a great deal of the cost of one health examination resides in expended man-hours. Further, since the measured data are recorded manually, the overall process is inefficient and relatively slow, and furthermore, recording errors and misreading of recorded data are apt to occur.

SUMMARY OF THE INVENTION

It is a first object of the present invention to reduce the number of staff members required for conducting a periodic health examination and to cut the costs of the health examination.

It is a second object of the present invention to prevent recording mistakes and reading errors by eliminating manual recording of measured data. Moreover, it is a third object of the present invention to store the measured data of the various measuring instruments on a magnetic card, and to eliminate the manual recording for each measuring instrument, thereby shortening the time required for the health examination and improving the efficiency of the health examination.

In order to achieve the aforementioned objects, the respective measuring instruments for height, weight, blood pressure, eyesight, hearing, and urine content are completely automated and provided with magnetic card read/write devices. The measured test data of the measuring instruments is stored on a magnetic card which is inserted into a reader after the completion of the measurements. The read measured data is then displayed. A doctor conducts a diagnosis with reference to a permanent examination card, a questionnaire completed in advance by the person to be examined and the displayed measured data. The diagnostic result of the doctor is printed out on the examination card and stored, if necessary, in a storage disc medium.

BRIEF DESCRIPTION OF THE DRAWINGS

The present invention is described in the following with reference to the accompanying drawing, wherein.

DETAILED DESCRIPTION OF THE INVENTION

Figure 1:
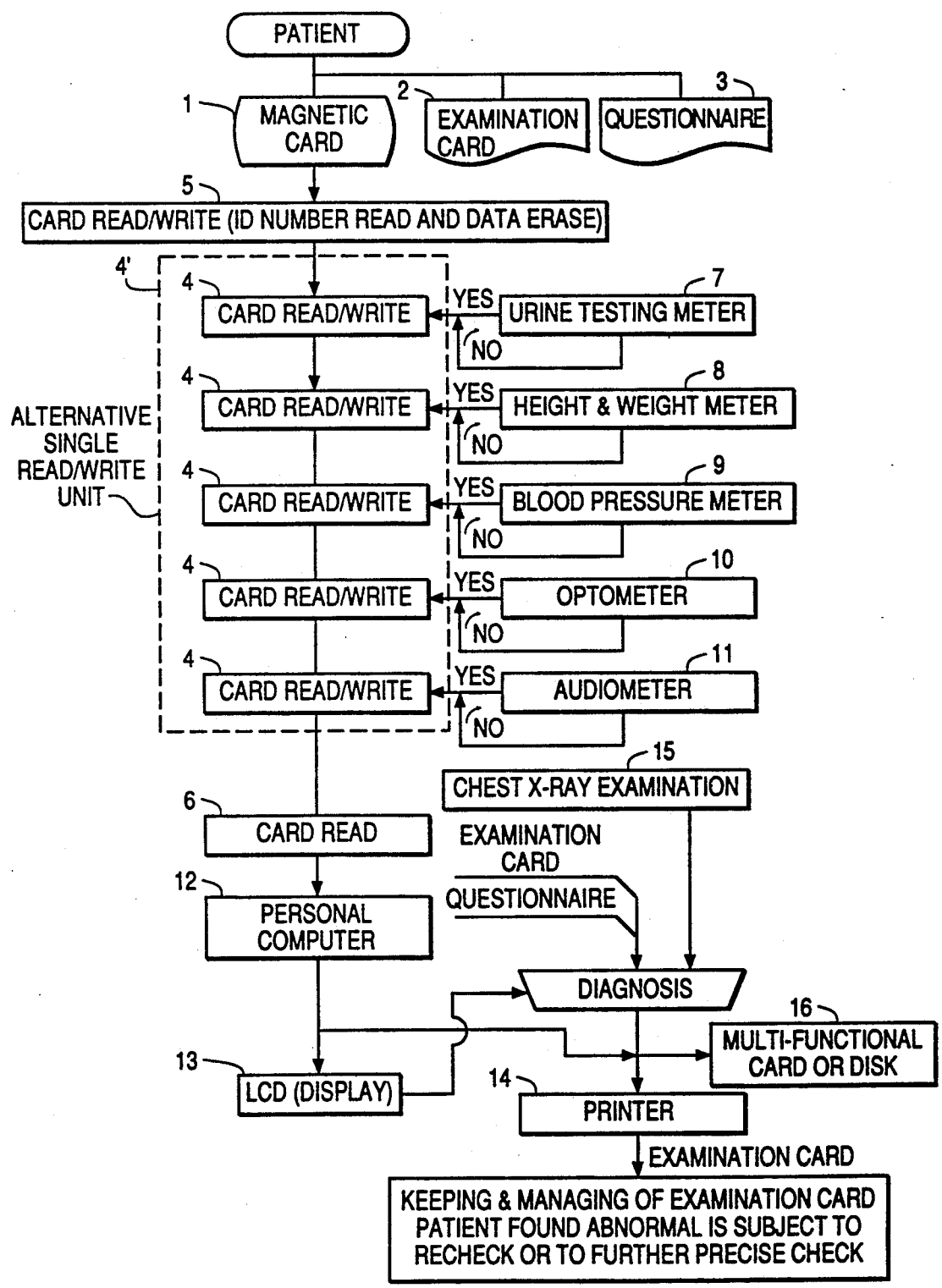
FIG. 1 is a system flow chart showing the configuration of a method and apparatus of the present invention.

The present invention has been devised to achieve the aforementioned objects. The present invention will now be described in detail with reference to the accompanying drawings.

The present invention employs a multi-functional storage device, such as the magnetic card 1 shown in FIG. 1. The magnetic card 1 is a well-known plastic card having magnetic stripes formed thereon. Reference numeral 2 denotes an examination card which is maintained for each patient continuously for a specified period as may be required by local safety and health laws. Reference numeral 3 denotes a questionnaire which is handed out at the health examination to each person to be examined together with the magnetic card 1 and the examination card 2. The questionnaire 3 is filled in beforehand by the person to be examined to obtain necessary information such as past illnesses and subjective and/or objective symptoms.

Reference numeral 4 denotes read/write (R/W) devices respectively provided in association with various testing stations 7, 8, 9, 10 and 11. Each read/write device 4 stores respective measured data on the magnetic card 1. Each read/write device 4 incorporates a known computer and functions such that, when the magnetic card 1 is inserted via an inlet of the read/write device 4 and when the person to be examined operates the testing stations 7, 8, 9, 10 and 11 according to appropriate operating instructions, measured data are stored on the magnetic card 1. When the storing of measured data on the magnetic card 1 is complete, the respective read/write device 4 dispenses the magnetic card 1. It is noted that a single read/write unit 4 can be provided for all the testing stations 7, 8, 9, 10 and 11.

Reference numeral 6 denotes a separately installed read device which functions as a reader and is connected to computer 12 having a display 13 such as a liquid crystal display (LCD) and a printer 14. When the magnetic card 1, having the various measured data stored thereon by the read/write devices 4, is insert in an inlet of the read device 6 after completion of all measurements at the testing stations 7, 8, 9, 10 and 11, a doctor operates the computer 12 so that the measured data stored on the magnetic card 1 is displayed on the display 13 and printed out on the examination card 2 by the printer 14.

Reference numeral 5 denotes a read/write device which deletes selected data stored on the magnetic card 1 and which automatically reads a stored variable examination number to be printed as a certification (ID) number. The read/write device 5 functions such that, when the magnetic card 1 is insert into an inlet of the read write device 5, previous data remaining on the magnetic card 1 is deleted and the examination number of the person to be examined is automatically printed.

Turning now to the various test stations, reference numeral 7 denotes a urine tester which automatically measures urobilinogen, sugar, protein and other urinary properties, and by changing of a test paper, a pH, latent blood, ketone body, nitrite etc. can also be measured. In this case, the person to be examined places a paper cup filled with urine in the urine tested 7 according to appropriate operating manual instructions, and inserts the magnetic card 1 into the read/write device 4 to automatically record the measured data on the magnetic card 1.

Reference numeral 8 denotes a height and weight meter, whereby, in accordance with operating instructions, each person to be examined inserts the magnetic card 1 into the read/write unit 4 and stands on the meter 11 which measures the person's height and weight and automatically records the measured data on the magnetic card 1. It is also possible to optionally indicate a person's relative fatness using the measured height and weight data.

Reference numeral 9 denotes a sphygmomanometer which operates such that, when an arm is inserted into the sphygmomanometer 9 according to operating instructions, maximum and minimum blood pressure and pulse rates, together with measuring time data, are recorded automatically on the magnetic card 1.

Reference numeral 10 denotes an optometer including a distance switching device for switching a test distance between 33 cm and 5 meters and a voice annunciator. The optical exam takes place in response to instructions of the voice annunciator and resultant test data is recorded on the magnetic card 1.

Reference numeral 11 denotes an audiometer, in which a hearing frequency may be selected and a hearing capability measured in the range of 10 to 100 decibels (dB) according to operating manual instructions. The thus measured hearing data is then stored on the magnetic card 1 via the read/write device 4 in the same manner as effected at the other test stations.

Provisions may also be adopted for conducting a chest x-ray examination by a radiographer using a known x-ray apparatus 15. In the case where an abnormality is found, the result is recorded on the examination card for later diagnosis.

The display 13 displays the measured data stored on the magnetic card 1. The doctor conducts a diagnosis by comparing such display data with information contained on the examination card and the questionnaire. The diagnosis opinion and the measured data are printed on the examination card 2 using the printer 14 by operating a keyboard of the computer 12. When necessary, such information may be recorded on a storage medium such as a magnetic or optical disc 16 via the computer 12. The desired health examination is thereby complete.

In the embodiment of the present invention, since the person to be examined inserts the magnetic card 1 and operates the various test stations according to operating instructions, the various measurements can be easily performed and the health examination can be effected using one staff member rather than the ten staff members hitherto required. In addition to the diagnosis effected by comparing and evaluating the measured data displayed on the display 13, the permanent examination card 2 having the previous examination results and the questionnaire 3 completed in advance by the person to be examined, the doctor can effect a more comprehensive diagnosis by palpation.

Since the recording is effected by the computer 12 using the printer 14 and possibly the disc medium 16, the printing and storing can be performed rapidly without manual writing and reading errors. Thus, the overall efficiency of the health examination is improved considerably.

Furthermore, as an alternative embodiment of the present invention, the various test stations 7 to 11 may be commonly connected to a single read/write device 4'. In such a case, the magnetic card 1 is inserted at the beginning of the examination and successively recorded with the measurement data of each test station. As such, the magnetic card 1 is not repeatedly insert and taken out of the respective read/write devices 4 of the test stations, thereby increasing the speed of the examination. The magnetic card 1 having all the data recorded, thereon is dispensed from the single read/write unit 4' after completion of all the measurements of the test stations 7 to 11.

What is claimed is:

1. A method of conducting and recording a health examination of a patient using a minimal number of staff members, comprising:

a step of issuing the patient a magnetic card and a questionnaire and having the patient complete the questionnaire;

a step of testing the patent by having the patient conduct a plurality of health related self-test measurements at respective automated test stations, wherein at each automated test station the patient conducts the corresponding self-test measurement without the aid of a staff member;

a step of recording data results of the plurality of self-test measurements on the magnetic card;

a step of reading the data results of the plurality of self-test measurements from the magnetic card;

a step of conducting a diagnosis of the patient based on the data results of the plurality of self-test measurements and information contained in the questionnaire which has been completed by the patient; and, a step of creating a permanent record of the diagnosis and the data results of the plurality of self-test measurements.

2. A method as recited in claim 1, wherein said testing step includes having the patient insert the magnetic card into a respective magnetic card write device provided at each of the automated test stations, and wherein said step of recording data results is conducted at each of said automated stations.

3. A method as recited in claim 2, further comprising assigning the patient an examination card, wherein said creating step includes printing the diagnosis and the data results of the plurality of self-test measurements on the examination card associated with the patient.

4. A method as recited in claim 2, further comprising providing a disc recording medium, wherein said creating step includes recording the diagnosis and the data results of the plurality of self-test measurements on the disc recording medium.

5. A method as recited in claim 2, further comprising, prior to said testing step, a step of erasing data contents stored on said magnetic card.

6. A method as recited in claim 1, further comprising assigning the patient an examination card, wherein said creating step includes printing the diagnosis and the data results of the plurality of self-test measurements on the examination card associated with the patient.

7. A method as recited in claim 1, further comprising providing a disc recording medium, wherein said creating step includes recording the diagnosis and the data results of the plurality of self-test measurements on the disc recording medium.

8. A method as recited in claim 1, further comprising, prior to said testing step, a step of erasing data contents stored on said magnetic card.

9. A health examination system for conducting and recording a health examination of a patient using a minimal number of staff members, comprising:
   a plurality of test stations each including (a) test means for the patient to conduct a health related self-test measurement without the aid of a staff member, and (b) a magnetic card read/write means for writing results of the health related self-test measurement onto a magnetic card assigned to the patient; and,
   a diagnostic station including (a) read means for reading a plurality of health related self-test measurements store don the magnetic card assigned to the patient, and (b) means for creating a permanent record of a diagnosis of the patient and the plurality of health related self-test measurements.

10. A system as recited in claim 9, wherein said creating means includes a printer means for printing the diagnosis and the plurality of health related self-test measurements onto an examination card.

11. A system as recited in claim 10, further comprising means for erasing data stored on said magnetic card prior to using said magnetic card at said plurality of test stations.

12. A system as recited in claim 9, wherein said creating means includes a disc storage means for recording the diagnosis and the plurality of health related self-test measurements onto a disc recording medium.

13. A system as recited in claim 12, further comprising means for erasing data stored on said magnetic card prior to using said magnetic card at said plurality of test stations.

14. A system as recited in claim 9, further comprising means for erasing data store don said magnetic card prior to using said magnetic card at said plurality of test stations.

* * * * *